United States Patent
Rowhani et al.

(10) Patent No.: US 10,241,072 B2
(45) Date of Patent: Mar. 26, 2019

(54) ELECTROCHEMICAL SENSORS FOR TESTING WATER

(71) Applicant: Arch Chemicals, Inc., Allendale, NJ (US)

(72) Inventors: Touraj Rowhani, Alpharetta, GA (US); Steven Sungil Jang, Cumming, GA (US)

(73) Assignee: ARCH CHEMICALS, INC., Allendale, NJ (US)

( * ) Notice: Subject to any disclaimer, the term of this patent is extended or adjusted under 35 U.S.C. 154(b) by 733 days.

(21) Appl. No.: 14/033,795

(22) Filed: Sep. 23, 2013

(65) Prior Publication Data

US 2014/0083865 A1  Mar. 27, 2014

Related U.S. Application Data

(63) Continuation-in-part of application No. 14/032,891, filed on Sep. 20, 2013.

(60) Provisional application No. 61/704,139, filed on Sep. 21, 2012.

(51) Int. Cl.
*G01N 27/403* (2006.01)
*G01N 27/416* (2006.01)

(52) U.S. Cl.
CPC ....... *G01N 27/403* (2013.01); *G01N 27/4166* (2013.01)

(58) Field of Classification Search
None
See application file for complete search history.

(56) References Cited

U.S. PATENT DOCUMENTS

| | | | |
|---|---|---|---|
| 4,176,032 A | 11/1979 | Stevenson, Jr. | |
| 5,031,449 A * | 7/1991 | Kuwana | G01N 30/64 204/294 |
| 5,483,164 A | 1/1996 | Moss et al. | |
| 2002/0179442 A1* | 12/2002 | Miyazaki | C12Q 1/003 204/403.01 |

(Continued)

FOREIGN PATENT DOCUMENTS

WO    2009/135270 A1    11/2009

OTHER PUBLICATIONS

Pei et al. (J. Nanotechnol. Eng. Med. Aug. 2013, vol. 4, pp. 031003-1-031003-5).*

(Continued)

*Primary Examiner* — Gurpreet Kaur
*Assistant Examiner* — Steven E Rosenwald
(74) *Attorney, Agent, or Firm* — Lucas & Mercanti, LLP

(57) ABSTRACT

An electrochemical sensor for the detection and analysis of an analyte in a solution is disclosed. The electrochemical sensor has an electrically non-conductive support; a plurality of electrodes on the support, each electrode formed from an electrode material and having a first surface and an opposite second surface, said first surface facing towards the support and the second surface facing away from the support. The plurality of electrodes includes a reference electrode, a counter electrode, and a working electrode. The working electrode has a reagent composition containing a reagent for detecting an analyte applied directly to the second surface of the working electrode or dispersed throughout the electrode material of the working electrode.

6 Claims, 4 Drawing Sheets

(56) References Cited

U.S. PATENT DOCUMENTS

2009/0255811 A1* 10/2009 Forrow ................ C12Q 1/001
 204/403.14
2009/0321278 A1 12/2009 Birch et al.
2012/0168308 A1 7/2012 McCormack et al.

OTHER PUBLICATIONS

Pei et al. (J. Nanotech. Eng. Med. 2013, 4, 031003-1-5).*
Szabo et al. (International Journal of Corrosion, Article ID 756950, 2010).*
Seifer (Russian Journal of Coordination Chemistry, 28/5, pp. 301-324, 2002).*
Prabhu et al. (Anal. Chem. 1989, 61, 2258-2263) (Year: 1989).*
Shaick et al. (Journal of Bangladesh Chemical Society, vol. 24(2), 158-164, 2011) (Year: 2011).*

* cited by examiner

ELECTROCHEMICAL SENSORS FOR TESTING WATER

CROSS REFERENCE TO RELATED APPLICATIONS

This application is a continuation-in-part of U.S. patent application Ser. No. 14/032,891 filed Sep. 20, 2013, which is in turn claims priority under 35 U.S.C. § 119(e) from Provisional Application Ser. No.: 61/704,139 filed Sep. 21, 2012, the disclosures of each of which are incorporated herein by reference.

FIELD OF THE INVENTION

The present invention relates to an electrochemical sensor for detection and analysis of one or more analytes in water.

BACKGROUND OF THE INVENTION

Chemicals have been added to pools and other water supplies to disinfect and sanitize the water so that the quality of the water is useable for its intended purpose. There are a number of factors that affect water quality, including water chemistry parameters. The major chemistry parameters that are associated with maintaining water quality includes free available chlorine, total available chlorine, total hardness, total alkalinity, pH, cyanuric acid, as well as copper. It is therefore important to monitor and control these chemistry parameters for water quality management, especially for water such as recreational and industrial water.

Chlorine disinfects or sanitizes water by destroying harmful microorganisms, such as bacteria, fungi, and viruses and also controls nuisance organisms, including algae that may be occur in recreational water, filtration device, and piping. Available chlorine is the major component of chlorine species, which is mainly composed of a class of chemicals that produce hypochlorous acid (HOCl), when is dissolved in water. When chlorine, either as gaseous chorine, sodium hypochlorite, or calcium hypochlorite dissolves in water it produces HOCl, and at the pH range of 5-6 chlorine exists as HOCl:

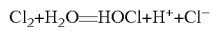

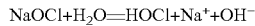

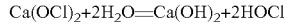

The hypochlorous acid may then dissociate into hydrogen ions (H$^+$) and hypochlorite ions (OCl$^-$) and the hypochlorite ions (OCl$^-$) become more predominant at higher pH of 7.2-7.5.

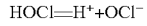

Chlorine in the forms of Cl$_2$, HOCl, or OCl$^-$ is known as free available chlorine, and these three forms of chlorine may present in water and their relative amounts in water depends on pH and to a slight extent on temperature.

Combined available chlorine refers to any chlorine species associated with inorganic chloramines (NH$_2$Cl and NHCl$_2$) and organic chloramines (RNHCl, R=alkyl) in water. Total available chlorine is the sum of free available chlorine and combined available chlorine. The relative amount of combined available chlorine also depends on pH and temperature, and the concentration of inorganic or organic amines in water. However, the combined chlorine undergoes limited hydrolysis in water and has less oxidizing power than free available chlorine. It is therefore important to distinguish free available chlorine and combined available chlorine to measure the disinfection strength of residual chlorine.

Total hardness is the measure of water hardness. Calcium and Magnesium ions are the primary sources of water hardness. In general, calcium represents about 97% of the water hardness in pool water and the level of dissolved calcium is kept ideally between 200 to 500 ppm. Pool water requires the appropriate level of water hardness. High calcium hardness can result in cloudy water and scale formation due to the precipitation of calcium carbonate from the water, whereas low calcium can lead to corrosion.

Total alkalinity is the measure of the pool water's buffering capacity to resist pH change. The buffering capacity of alkalinity in water is due to carbonate, bicarbonate, hydroxide, and sometimes borates, silicates and phosphate, but is mainly measured by the amount of carbonate and bicarbonate in pool water. Further, at a desirable pH range of 7.2-7.6 in pool water most of the carbonate ions are in the bicarbonate ions from which buffering is provided. In general, total alkalinity is kept between 60-150 ppm depending on the sanitizing system being used and without a proper control of total alkalinity pH of the water rises or falls abruptly, causing the water to form scale and becomes cloudy or corrosive. The level of total alkalinity is tested and adjusted before adjusting pH.

Cyanuric acid content in pool water is important because cyanuric acid is functioning as free available chlorine stabilizer in water by protecting the free available chlorine against UV light degradation. Thus, maintaining sufficient cyanuric acid levels in water is important for maintaining sufficient levels of free available chlorine.

There are a number of sources for copper to enter the pool water including different water sources and algaecide, and dissolved copper can lead many pool water issues and public concerns. For example, high level of copper can result in ugly staining. Thus, keeping the level of dissolved copper in the pool water as low as possible is important for maintaining water quality.

There is a continuous interest in developing simple, rapid, and reliable methods for the determination of water chemistry parameters including, but not limited to, free chlorine, total chlorine, total hardness, total alkalinity, pH, cyanuric acid and copper. For example, because chlorine species in water are very reactive and may dissipate very quickly the reliable and accurate measurements of residual chlorine in water are difficult. There are a number of field test kits available for the determination of free and combined available chlorine in water, which is mostly based on the use of DPD (diethyl p-phenylenediamine). DPD test kits are manufactured with either liquid, powder or tablet reagents. Test kits that are currently available for the analysis of water hardness and total alkalinity are based on the use of specific dye reagents or acid-base indicators, followed by the spectrometric analysis or titration where changes in color in test solution are monitored. However, there are often interferences and human error in monitoring the color change for testing for hardness or alkalinity in water, leading to erroneous test results. At present, there are no simple, rapid, cost effective and reliable diagnostic test kits or devices to accurately and easily measure the contents of free chlorine, total chlorine, total hardness, and total alkalinity in recreational water. The present invention provides an answer to that need.

SUMMARY OF THE INVENTION

In one aspect, the present invention provides an electrochemical sensor for detection and analysis of an analyte in a solution. The electrochemical sensor has an electrically non-conductive support; a plurality of electrodes on the support, each electrode formed from an electrode material and having a first surface and an opposite second surface, said first surface facing towards the support and the second surface facing away from the support. The plurality of electrodes includes a reference electrode, a counter electrode, and a working electrode. The working electrode has a reagent composition containing a reagent for detecting an analyte applied directly to the second surface of the working electrode or dispersed throughout the electrode material of the working electrode.

The electrochemical sensor of the present invention may have working electrodes for the detection and analysis of water for free chlorine, total available chlorine, total alkalinity, total hardness of the water, pH, cyanuric acid and copper.

In another embodiment of the present invention is directed to method of analyzing water. The method includes placing the electrochemical sensor in a display device and placing the electrodes of the sensor in water to be analyzed.

These and other aspects will become apparent when reading the detailed description of the invention.

DETAILED DESCRIPTION OF THE PREFERRED EMBODIMENTS

Figure 1:
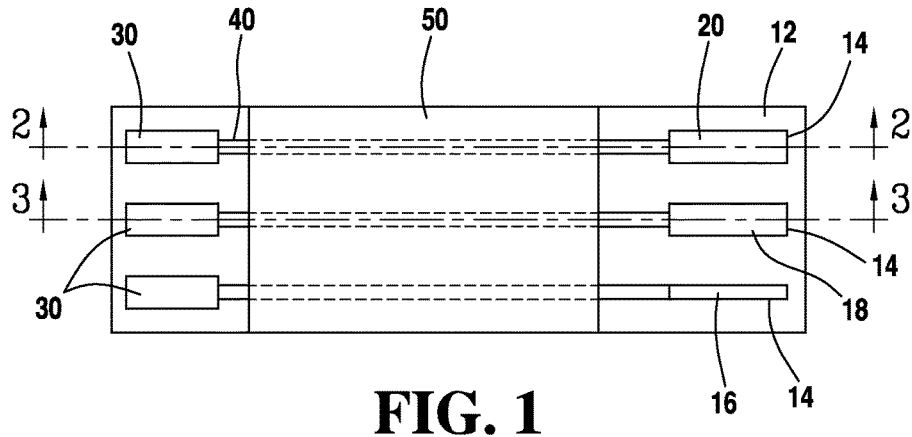
FIG. 1 shows a top plan view of the electrochemical sensor having a single working electrode.

To gain a better understanding of the present invention, attention is directed to the drawings. The drawings are not intended to be limiting but are intended for understating the present invention. It has now been surprisingly found the electrochemical sensor of the present invention is able to perform without the need of (i.e., omits) an intermediate layer between the electrode and the reagent composition. It has been found that the sensor of the present invention has simplicity of manufacture and has sensitivity to give a sensor with reproducible results.

Figure 2:
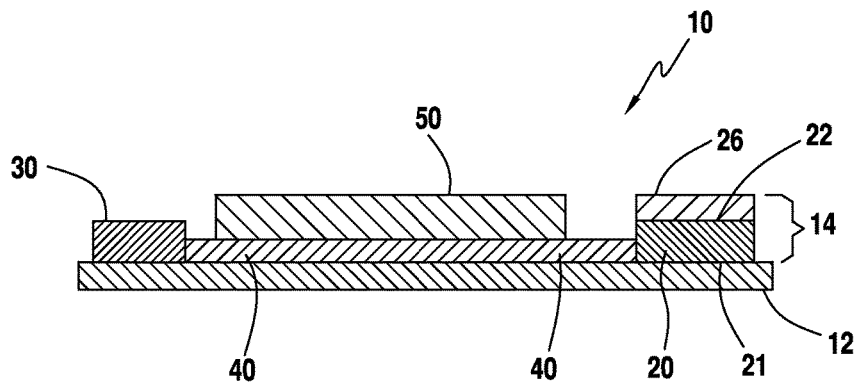
FIG. 2 shows an exaggerated cross-sectional side view of the electrochemical sensor along section line 2-2 viewing the working electrode with the reagent composition deposited on the electrode.
Figure 2A:
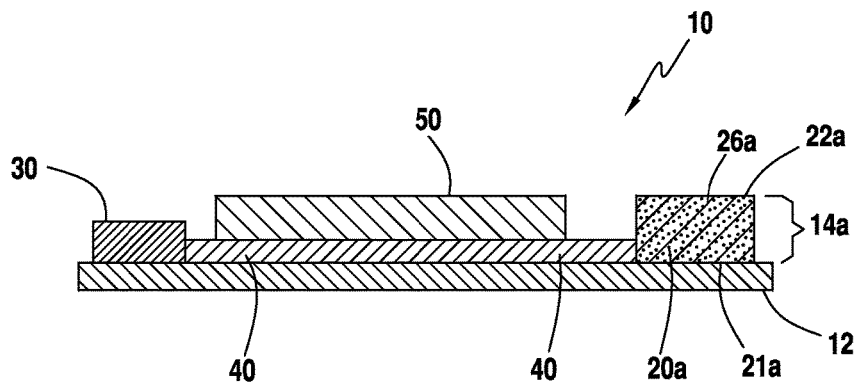
FIG. 2A shows an exaggerated cross-sectional side view of the electrochemical sensor along section line 2-2 viewing the working electrode with the reagent composition dispersed throughout the electrode material instead of deposited on the electrode as shown in FIG. 2.
Figure 3:
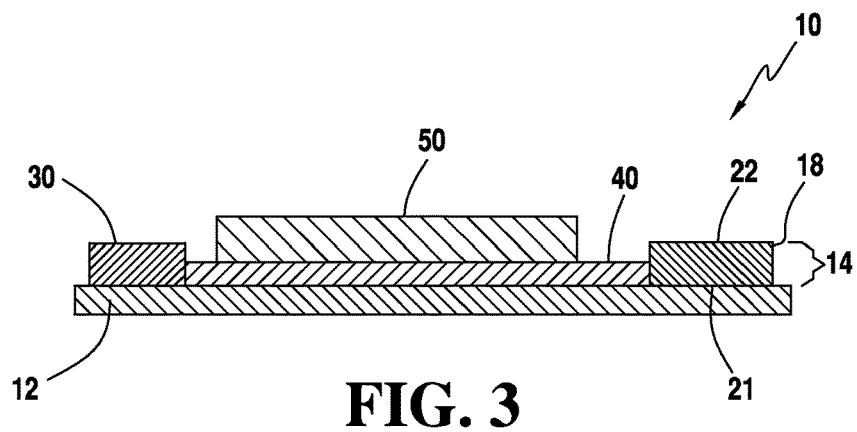
FIG. 3 shows an exaggerated cross-sectional side view of the electrochemical sensor along section line 3-3 viewing the counter electrode.

Turning to FIG. 1, shown is a top view of the electrochemical sensor 10. The electrochemical sensor 10 has a support 12 which has a plurality of electrodes 14 disposed on support 12 and formed from an electrode material. The electrodes 14 may be disposed on both sides of the support or only on one side of the support. The electrodes 14 are spaced about a suitable distance so that the electrodes 14 are independent from each other. Electrodes 14 include a reference electrode 16, a counter electrode 18 and a working electrode 20. Operation of each of these electrodes will be described in more detail below. As can be seen in FIGS. 2 and 3, each electrode 14 has a first surface 21 adjacent support 12 and a second surface 22, which is opposite the first surface 21 and the second surface 22 faces away from the support 12. As can be also seen in FIG. 2, electrode 14 includes working electrode 20 with reagent composition 26 directly deposited on (i.e., applied to) second surface 22. In another embodiment, as seen in FIG. 2A, electrode 14A includes working electrode 20A with first surface 21A and opposite second surface 22A. As can be seen further in FIG. 2A, working electrode 20A has reagent composition 26A dispersed throughout the electrode material instead of being directly deposited on second surface 22A.

The support 12 also has plurality of connectors 30 disposed thereon, which serve to connect the electrochemical sensor to an instrument, which will allow a user of the electrochemical sensor 10 to take readings from the sensor. The connectors 30 are generally on the same surface of the support 12 as electrodes 14, but are generally positioned away from the end of the support containing electrodes 14. It is possible for the connectors 30 to be on the opposite end of the support from the electrodes 14, as is shown in FIG. 1, or, in the alternative, connectors 30 may be located along the sides of the support 12.

The electrodes 14 are each separately electrically connected to separate connectors 30. Each electrode 14 may be directly connected to a connector 30, or may be connected via a conductive track 40 which is disposed on the support 12. Each conductive track 40 serves to connect a given connector 30 to a given electrode 14, without crossing another conductive track 40. To protect the conductive tracks 40, a protective coating 50 is optionally applied over the support 12, in all or most of the area in which the conductive tracks 40 are present.

Support 12 is prepared from a material which is electrically non-conductive and inert to the testing environment and chemicals applied thereto to form the electrodes 14, the connectors 30 and the conductive tracks 40. Suitable materials useable for the support include, for example, ceramic, paper, plastic or glass materials. Generally, from a standpoint of cost and durability, the support 12 is generally flexible to a degree so that the support 12, electrodes 14, connectors 30 and conductive tracks 40 are not damaged due to handling prior to use. Generally, support 12 is prepared from a dielectric plastic material. Exemplary plastic materials usable for the support include polyester, polycarbonate and polyvinylchloride. Other polymeric plastic materials may also be used without departing from the scope and spirit of the present invention. Ideally, the support should have a cost associated therewith which allows the sensor to be disposable after use.

The electrodes 14 may be disposed on the support using any of a variety of techniques known to those skilled in the art. Suitable techniques include, for example, screen printing, lithography, vapor deposition, spray coating, vacuum deposition, inkjet printing or other similar techniques. Each electrode 14 is prepared from a conductive composition which is applied to the support 12. Suitable conductive compositions include conductive inks with may be screen printed or inkjet printed onto the support 12. Conductive inks include inks that contain conductive particles in the ink. Exemplary conductive particles include metal particles of conductive metals, such as gold, silver, platinum and conductive noble metal, carbon particles or other similar conductive polymers. In one embodiment of the present invention, the materials that may be used for the counter electrode 18 and the working electrode 20 include carbon, metal or metal-carbon mixture. A silver based ink or a silver/silver chloride based ink may be used for the reference electrode 14. Generally, silver/silver chloride based inks are used for the reference electrode 14.

The connectors 30 may be prepared from any conductive material including copper, gold, silver, platinum or other similar conductive metals. Generally, the connectors 30 will be prepared from the same ink material used to prepare one or more of the electrodes, from an ease of manufacture standpoint. In one embodiment of the present invention, the connectors 30 are each prepared from the same material used to prepare the reference electrode 14. For example, the connectors may be prepared form a silver/silver chloride based ink.

The connecting tracks 40, when present, are also prepared from a conductive ink and is applied using the same techniques mentioned above for the disposition of the electrodes to the substrate. Generally, the connecting tracks 40 will be prepared from the same ink material used to prepare the connectors 30 or electrodes 14. By using the same material, the sensor can be quickly and easily manufactured. In one embodiment, the connecting tracks are prepared from a silver/silver chloride based ink.

To protect the connecting tracks 40 from damage prior or during use, and to prevent the connecting tracks 40 from acting like a reference electrode, if they come into contact with the water to be tested, connecting tracks 40 may be provided with a protective insulation coating 50. Protective insulation coating 50 can be prepared from any electrically non-conductive material that will effective adhere to the support 12 and the conductive tracks 40. Exemplary materials include, for example, dielectric polymeric materials such as polyesters, polyvinyl chloride and other similar compatible polymers. It is noted that the protective coating does not need to cover the entirety of the connecting tracks 40, but will need to cover the connecting tracks where the connecting tracks 40 connect to the electrodes 14. This will prevent the connecting tracks 40 from coming into contact with the water to be tested, as the electrodes 14 are placed in the water to be tested.

Figure 4:
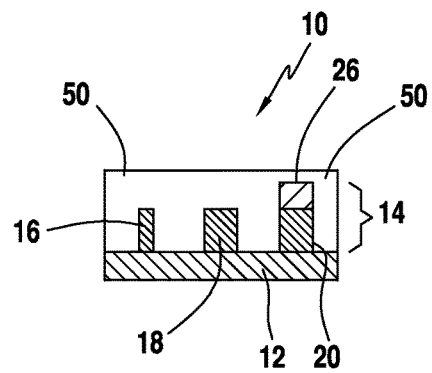
FIG. 4 shows an exaggerated cross-sectional front view of the electrochemical sensor along section line 4-4 viewing the electrodes with the reagent composition deposited on the electrode.

In the present invention, reference electrode 16 and counter electrode 18 are prepared from different materials. Generally, working electrode 20 is prepared from the same material as the counter electrode 18; however, working electrode 20 has a reagent composition 26 applied to the second surface 22 of the working electrode 20, as is shown in FIG. 2, which show a cross-section of the electrochemical sensor 10, along section line 2-2 in FIG. 1. Alternatively, the working electrode (shown as 20A in FIG. 2A) has the reagent composition (shown as 26A) mixed with electrode material making up the working electrode to disperse reagent composition 26A throughout working electrode 20A. The reagent composition 26 applied to the working electrode 20, or mixed with the electrode material, determines the analyte that the working electrode 22 will detect and analyze. Comparing the cross-section of the electrochemical sensor along the working electrode 20 shown of FIG. 2 to the cross-section of electrochemical sensor along the counter electrode 18 shown in FIG. 3, it can be seen that the counter electrode 18 does not have a reagent composition 26 applied thereto, while working electrode 20 does. FIG. 4 shows the front-side view of the electrochemical sensor 10 of the present invention. Again, it can be seen that the working electrode 20 has a reagent composition 26 applied to the second surface 22 of the working electrode 20. Alternatively, as can be seen in FIG. 2A, the reagent composition can be dispersed throughout the electrode material of the working electrode. It can also be seen that the reference electrode 16, the counter electrode 18 and the working electrode 20 are spaced apart on the support 12. This allows each of these electrodes to be electrically insulated from one another.

Figure 5:
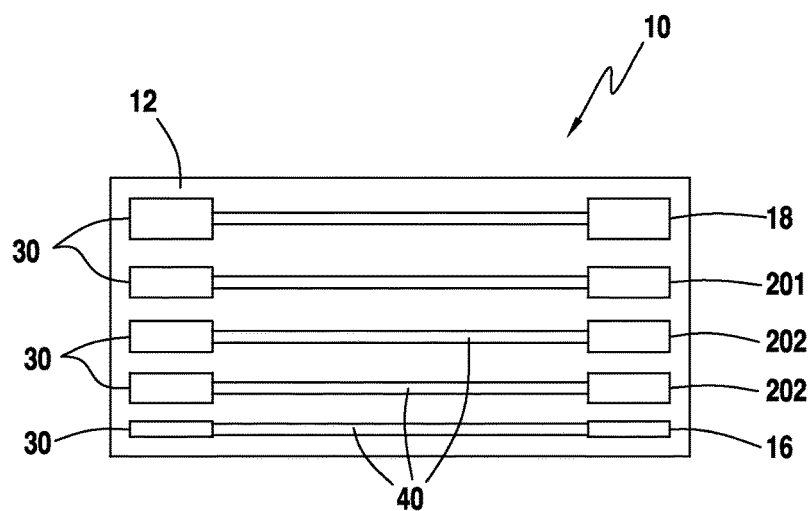
FIG. 5 shows a top plan view of the electrochemical sensor having a plurality of electrodes.

The reagent composition applied to, or dispersed within, the working electrode is modified with appropriate reagents for the individual detection of free chlorine, total chlorine, calcium hardness, pH, cyanuric acid, copper, or total alkalinity. Each working electrode will have a reagent composition applied to the second surface of that working electrode. The sensor 10 may have multiple working electrodes, as shown in FIG. 5. As can be seen in FIG. 5, there are multiple working electrodes 201, 202, 203. Each working 201, 202 and 203, may have a different reagent composition applied to the surface. Alternatively, when multiple working electrodes are present, two or more working electrodes may have the same reagent. When multiple working electrodes are present, the only limitation to the number of electrodes is the space available the surface of the support 12. It is contemplated that electrodes could be on both sides of the support. Generally, there will be between about 1 and about 8 working electrodes on the sensor.

Detection of each analyte is based on the amperometric or voltametric analysis using a specific reagent or reagent mixtures deposited on the working electrode, or mixed with the ink prior to screen printing the electrode on the substrate. The amperometric method is a controlled-potential electrochemical technique, where the current response to an applied potential is measured by a potentiostat. A potentiostat is an electronic instrument that controls the voltage difference between a working electrode and a reference electrode. Any type of commercially available or custom-made portable, field-deployable potentiostat may be used. In the case of labs, non-portable potentiostats may be used. An exemplary commercially available potentiostat is a Uniscan Instruments, Ltd. Model PG581 Potentiostat, having office in Buxton, United Kingdoms. It is also contemplated that other potentiostats, or other items such as smart phones with applications (software) could also function as a potentiostats for the electrochemical sensors of the present invention. In general, the sensor is polarized at a potential value (vs. Ag/AgCl) for a time period. The current observed at a given time is recorded and averaged using the software embedded in the potentiostat. The concentration of analyte is then determined using the average current value and the preloaded calibration table in the instrument.

The reagent compositions useable in the present invention will now be described.

Free Chlorine Detection Reagent Composition

The free chlorine reagent composition for the free chorine electrochemical sensor according to the invention, measures the content of free chlorine in water by the amperometric analysis. The reagent composition for the free chlorine electrochemical sensor will generally contain a redox indicator reagent, a buffer and a polymeric material. Typically, water is used as the solvent for the composition and the components are added so that the resulting composition has the component present in an amount disclosed below. These components are generally mixed and applied to the second surface of the working electrode. The solvent is removed by drying the composition at an elevated temperature for a period of time.

Suitable redox indicator reagents include, for example p-phenylenediamine salts, N,N-diethyl-p-phenylenediamine sulfate salt (DPD), N,N-dimethyl-p-phenylenediamine sulfate salt, and N,N,N'N'-tetramethyl-p-phenylenediamine. The redox indicator reagent component is added to the reagent composition to form a solution which is about 0.01 M to about 0.20 M, and more typically in a 0.03 to about a 0.07 M.

Suitable buffers include phthalate buffers, phosphate buffers. Phosphate buffers include, for example disodium hydrogen phosphate, sodium di-hydrogen phosphate, and mixtures thereof. The buffer component is generally present in the reagent composition in the range of about 0.01 to about 0.03 M.

Sodium chloride is generally added to the buffer in a concentration of about 0.3 to about 0.6 M. Typically, it is added in an amount of about 0.4 to about 0.5 M.

In addition, the reagent composition will also have a polymeric binding component added to assist disposition of the redox indicator reagent to the surface of the electrode. In addition, the polymeric material in the reagent composition is used to retain reagent and buffer mixture on the electrode surface, and stabilizing the response of electrochemical detection. Possible polymers include, for example, polyethylene glycol, sodium alginate, polyvinyl alcohol, or other similar polymers. Generally, polyethylene glycol is used for the free chlorine sensor. Typically, the polymer is added in an amount of about 0.1 to about 2.0% by weight, based on the volume of the solution.

In the electrochemical sensor containing a free chlorine reagent composition applied to the working electrode, the amount of free chlorine is measured by generating a voltage applied from the reference electrode and the resulting current from the working electrode is measured, according to the reaction shown below:

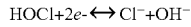
HOCl+2e- ↔ Cl⁻+OH⁻

The sensor is polarized at a potential value (vs Ag/AgCl) for a time period. The current observed at 15-30 seconds is averaged using the software embedded in the potentiostat. The concentration of free chlorine is then determined using the average current value and the pre-loaded calibration table in the instrument.

Total Chlorine Detection Reagent Composition

The total chlorine reagent composition for the total chorine electrochemical sensor according to the invention, measures the content of total chlorine in water by the amperometric analysis. The reagent composition for the total chlorine electrochemical sensor will generally contain a potassium halide salt, a buffer component and a polymeric material. Typically, deionized water is used as the solvent for the composition and the components are added so that the resulting composition has the component present in an amount disclosed below. These components are generally mixed and applied to the second surface of the working electrode to form the total chlorine working electrode.

The potassium halide salt added to the reagent composition may be potassium bromide, and potassium chloride. Generally, the potassium salt is added in an amount such that the potassium salt is present in a concentration of about of 0.05 to 2M typically about 0.25 to about 0.75 M. One specific example is a 0.5M concentration of potassium bromide.

Suitable buffers include phthalate buffers, phosphate buffers. Phosphate buffers include, for example disodium hydrogen phosphate, sodium di-hydrogen phosphate and mixtures thereof. Suitable phthalate buffers include potassium hydrogen phthalate. The buffer component is generally present in the reagent composition in the range of about 0.01 to about 0.3 M. The pH of the buffer solution should be adjusted to the range around 3-4 pH is generally adjusted using a diluted hydrochloric acid (HCl), such as 0.1 M HCl.

In addition, the reagent composition will also have a polymeric binding component added to assist disposition of the potassium salt and buffer to the surface of the electrode. In addition, the polymeric material in the reagent composition is used to retain reagent and buffer mixture on the electrode surface, and stabilizing the response of electrochemical detection. Possible polymers include, for example, polyvinyl alcohol, sodium alginate, or other similar polymers. Generally, sodium alginate is used is used for the total chlorine sensor. Typically, the polymer is added in an amount of about 0.1 to about 2.0% by weight, based on the weight of the solution.

Total chlorine is measured amperometrically by applying a voltage to the electrode and measuring the current from the working electrode. Combined chlorine is then determined by difference between the total chlorine and free chlorine contents. Potassium bromide can react with free chlorine and combined chlorine as follows:

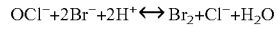
OCl⁻+2Br⁻+2H⁺ ↔ Br₂+Cl⁻+H₂O

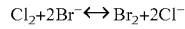
Cl₂+2Br⁻ ↔ Br₂+2Cl⁻

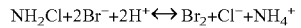
NH₂Cl+2Br⁻+2H⁺ ↔ Br₂+Cl⁻+NH₄⁺

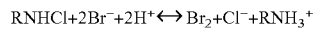
RNHCl+2Br⁻+2H⁺ ↔ Br₂+Cl⁻+RNH₃⁺

The liberated bromine is reduced electrochemically at the electrode as shown below:

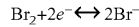
Br₂+2e⁻ ↔ 2Br⁻

Calcium Hardness Detection Reagent Composition

The calcium hardness sensor according to the invention measures the content of calcium ion in water by the amperometric analysis. The reagent used in the calcium hardness reagent composition is an electrochemical indicator for the detection of calcium ion and other complexometric indicators. The reagent composition for the hardness electrochemical sensor will generally contain an electrochemical indicator for the detection of calcium ion and other complexometric indicators, a buffer component and a polymeric material. Typically, deionized water is used as the solvent for the composition and the components are added so that the resulting composition has the component present in an amount disclosed below.

The electrochemical indicator for the detection of calcium ion and other complexometric indicators are generally present in the reagent composition in an amount in the range of about 1 to 10 mM, typically about 2-4 mM. Suitable compounds for this component include Alizarin Red, Alizarin Yellow CG, Alizarin Green, Alizarin Blue Black B, and Eriochrome Black T. Of these, Alizarin Red S (3,4-dihydroxy-9,10-dioxo-2-anthracenesulfonic acid sodium salt) is typically used as an electrochemical indicator for the detection of calcium ion.

Suitable buffers include phthalate buffers, phosphate buffers and an acetate buffer. Phosphate buffers include, for example disodium hydrogen phosphate, sodium di-hydrogen phosphate and mixtures thereof. Suitable phthalate buffers include potassium hydrogen phthalate. The buffer component is generally present in the reagent composition in the range of about 0.01 to about 0.3 M. The pH of the buffer solution should be adjusted to the range around 3-4 pH is generally adjusted using a diluted hydrochloric acid (HCl), such as 0.1M HCl.

In addition, the reagent composition will also have a polymeric binding component added to assist disposition of the Alizarin Red S, and buffer to the surface of the electrode. In addition, the polymeric material in the reagent composition is used to retain reagent and buffer mixture on the electrode surface, and stabilizing the response of electrochemical detection. Possible polymers include, for example, polyvinyl alcohol, polyvinylpyrrolidone, sodium alginate, or other similar polymers. Generally, sodium alginate or polyvinyl alcohol are used is used for the calcium hardness sensor. Typically, the polymer is added in an amount of about 0.05 to about 5.0% by weight, based on the weight of the solution. More preferably, the polymer is added in an amount of about 1.5 to 3% by weight, based on the weight of the solution.

Suitable buffers include phthalate buffer, phosphate buffer, and acetate buffer in a pH range of 3.0 to 4.0. Suitable polymer materials may include, but not limited to sodium alginate, polyvinyl alcohol, polyvinylpyrrolidone or other polyelectrolytes.

In another embodiment, the calcium hardness reagent is a copper (II) salt pre-mixed with a cationic ion exchange resin in lieu of a buffer and alizarine Red S. The copper/resin mixture is combined with a polymeric material, as described above, to prepare the reagent composition.

In another embodiment, the measurement of calcium ions in water is made by the electrochemical detection of copper (II) ion that is released from cation exchange resin via ion exchange reaction. Copper salts in anhydrous or hydrated form are used as the source of copper (II) ions. Possible copper (II) salts include, but are not limited to, copper sulfate, copper chloride and copper nitrate. Copper (II)-bound cation exchange resin is prepared by soaking the resin in appropriate copper salt solution, drying the treated resin, and milling into fine powder. The powered exchange resin is then mixed with a polymeric binder, as described above, to prepare the reagent composition.

Suitable cation exchange resins include cation exchange resins commonly made of styrene and cross-linking agent divinyl benzene, which are post-functionalized to contain sulfonic acid groups, carboxylic acid groups, or their corresponding salts. Suitable cation exchange resins used to prepare the calcium hardness sensor include cation exchange resins sold under the trade names Amberlite®, Amberlist®, Dowex®, Duolite® that bear sulfonic acid or carboxylic acid groups, or their corresponding $Na^+$ or $H^+$ salt form.

Total Alkalinity Detection Reagent Composition

The total alkalinity sensor according to the invention measures the contents of carbonate and bicarbonate in water by the amperometric analysis using manganese compound as the reagent. Suitable manganese compounds include, for example, manganese (II) salts, including but not limited to manganese perchlorate, manganese acetate, manganese chloride, manganese nitrate, manganese sulfate. Typically, the reagent composition manganese (II) perchlorate as the reagent and a polymeric material. The manganese (II) perchlorate reagent is generally present in a concentration of 5 to 100 mM, typically between about 20 to 40 mM.

In addition, the reagent composition will also have a polymeric binding component added to assist disposition of the manganese (II) perchlorate to the surface of the electrode. In addition, the polymeric material in the reagent composition is used to retain reagent on the electrode surface, and stabilize the response of electrochemical detection. Possible polymers include, for example, polyvinyl alcohol, polyvinylpyrrolidone, sodium alginate, or other similar polymers. Generally, polyvinylpyrrolidone is used for the total alkalinity sensor. Generally, the polymer is added in an amount of about 0.5 to about 5.0% by weight, based on the volume of the solution. Typically, the polymer will be added in an amount of about 1.5 to about 3% by weight of the composition.

$Mn^{2+}$ ions complex with bicarbonate ions at a desirable pH range of 7.2-7.6 in pool water as shown below:

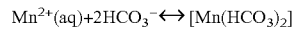

$$Mn^{2+}(aq) + 2HCO_3^- \leftrightarrow [Mn(HCO_3)_2]$$

The Mn-bicarbonate complex is then oxidized electrochemically at the electrode as shown below:

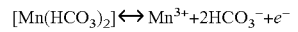

$$[Mn(HCO_3)_2] \leftrightarrow Mn^{3+} + 2HCO_3^- + e^-$$

Cyanuric Acid Detection Reagent Composition

The cyanuric acid sensor according to the invention measures the content of cyanuric acid in water by the amperometric analysis using transition metal (II) salts as the reagent. Suitable transition metals salts include, for example, sulfates, nitrates, and chlorides. Typically, the reagent composition contains copper sulfate as the reagent and a polymeric material. The copper sulfate reagent is generally present in a concentration of 5 to 100 ppm (as Cu), typically between about 5 to 20 ppm.

The reagent composition has a polymeric binding component added to assist binding of the transition metal salt (e.g., copper sulfate) to the surface of the working electrode. In addition, the polymeric binding material in the reagent composition is used to stabilize the response of electrochemical detection. Possible polymers include, for example, polyethylene glycol, polyvinyl alcohol, polyvinylpyrrolidone, or other similar polyelectrolyte polymers. Generally, polyvinyl alcohol is used to prepare the cyanuric acid sensor. Generally, the polymer is added in an amount of about 0.05 to about 5.0 by weight, based on the volume of the solution. Typically, the polymer will be added in an amount of about 0.05 to about 1% by weight of the composition.

Copper Ion Detection Reagent Composition

The copper ion sensor according to the invention measures the copper content in water by squarewave voltammetry using a buffer deposited on the working electrode. Typically, the buffer has pH ranging from 3 to 4, such as 3.5. Suitable buffers, for example, include phthalate, phosphate, citrate and acetate buffers with phthalate buffers being preferred.

Although not wishing to be bound by theory, it is believed that the polymeric electrolyte's in each of the reagent compositions functions to reduce the current passed by the working electrode and stabilize the signals to achieve sensitivity and consistency through creating plurality of working electrodes, via the creation of individual crystalline regions resulted from drying of reagents on top of the working electrode. Crystals formed in the polymer matrix by drying in the oven for specific amount of time and temperature. The polymer will act as a holding matrix for the crystals to be entrapped creating apertures of crystals on the surface of the electrode. Therefore, each crystal will act as a working electrode via a controlled dissolution of crystals and polymeric surface. The number and sizes of these apertures may be controlled by reagent concentration and drying time and temperature.

Other features may be present on the electrochemical sensor of the present invention. For example, an optional hood or cover may be placed over the electrodes to help protect the electrodes prior to use and to assist in holding the sample of water to be tested near the electrodes.

The shape of electrochemical sensors is generally rectangular in shape, as shown in FIGS. 1-5, but any other conventional shapes such as square or circular type shapes may also be used without departing from the scope of the present invention.

EXAMPLES

A. Preparation of Free Chlorine Sensor
Preparation of Free Chlorine Detection Reagent Solution A pH 7.4 buffer solution was prepared by dissolving 0.013 M of disodium hydrogen phosphate, 0.007 M sodium dihydrogen phosphate, and 0.45 M sodium chloride in deionized water. Then 1.33 wt. % polyethylene glycol (PEG) was added and dissolved in the solution. The solution was allowed to rest for 5 minutes and then 0.05 M N,N-diethyl-p-phenylenediamine sulfate salt (DPD) was added to the solution. The resulting mixture was shaken vigorously to dissolve the DPD into the solution.

Deposition Procedure

A portion of the solution was deposited on a carbon working electrode present on an electrochemical sensor having a reference electrode and a counter electrode. The total amount of the solution deposited on the working electrode was about 7.14 µL. Once deposition procedure was completed, the electrochemical sensor was carefully placed in an oven at 100° C. for 15 minutes. The sensor was removed from the oven and allowed to cool for a period of time of at least 5 minutes.

B. Preparation of Total Chlorine Sensor
Preparation of Total Chlorine Detection Reagent Solution A 0.1 M of potassium hydrogen phthalate pH 3.5 buffer solution was prepared in deionized water. To this solution was added 18% (v:v) of 0.1 M HCl. Then 0.03 g of sodium alginate per 15 mL of the buffer solution was dissolved in the solution. The solution was allowed to rest for 5 minutes at room temperature. Next, 0.5 M potassium bromide was added to the solution and the solution was vigorously shaken to dissolve the potassium bromide in the buffer solution.

The final deposition concentrations of the solution was: potassium hydrogen phthalate about 0.1 M, hydrochloric acid about 0.0176 M, potassium bromide about 0.5 M and sodium alginate about 0.2% (w:v).

Deposition Procedure

A portion of the total chlorine detection reagent solution was deposited on a carbon working electrode present on an electrochemical sensor having a reference electrode and a counter electrode. The total amount of the solution deposited on the working electrode was about 7.14 µL. Once deposition procedure was completed, the electrochemical sensor was carefully placed in an oven at 100° C. for 15 minutes. The sensor was removed from the oven and allowed to cool for a period of time of at least 5 minutes.

C. Preparation of Calcium Hardness Sensor
Preparation of Calcium Hardness Detection Reagent Solution A 0.1 M of potassium hydrogen phthalate buffer solution (pH 3.4) was prepared in deionized water. To this solution was added 18% (v:v) of 0.1 M HCl. Then 0.03 g of sodium alginate per 15 mL of the buffer solutions was dissolved into the solution. Then 0.03 g of sodium alginate was dissolved in the solution per 15 mL of the solution. The solution was allowed to rest for 5 minutes at room temperature. Next 0.003 M Alizarin Red S (3,4-dihydroxy-9,10-dioxo-2-anthracenesulfonic acid sodium salt) was added to the solution and to the solution was vigorously shaken to dissolve the Alizarin Red S into the buffer solution.

The final deposition solution concentrations of the solution was: potassium hydrogen phthalate about 0.1 M, hydrochloric acid about 0.0176 M, Alizarin Red S about 3 mM, and sodium alginate about 0.2% (w:v).

Deposition Procedure

A portion of the calcium hardness reagent solution was deposited on a carbon working electrode present on an electrochemical sensor having a reference electrode and a counter electrode. The total amount of the solution deposited on the working electrode was about 7.14 µL. Once the deposition procedure has been completed, the electrochemical sensor was carefully placed in an oven at 50° C. for 20 minutes. The sensor was removed from the oven and allowed to cool for a period of time of at least 5 minutes.

D. Preparation of Total Alkalinity Sensor
Preparation of Total Alkalinity Detection Reagent Solution The total alkalinity reagent composition was prepared by dissolving 2% by weight of polyvinylpyrrolidone (0.3 g/15 mL) in deionized water to prepare a solution. To this solution, 40 mM (152 mg/15 mL) of $Mn(ClO_4)_2 \cdot 6H_2O$ was added. The mixture was shaken until the components were dissolved. The resulting solution was the total alkalinity reagent solution.

Deposition Procedure

A portion of the total alkalinity reagent solution was deposited on a carbon working electrode present on an electrochemical sensor having a reference electrode and a counter electrode. The total amount of the solution deposited on the working electrode was about 7.14 µL. Once deposition procedure was completed, the electrochemical sensor was carefully placed in an oven at 100° C. for 15 minutes. The sensor was removed from the oven and allowed to cool for a period of time of at least 5 minutes.

E. Preparation and Testing of Alternate Calcium Hardness Sensor
Preparation of Calcium Hardness Detection Reagent Suspension The calcium hardness reagent composition was prepared by dissolving 2% (w/w) polyvinyl alcohol (PVA) in deionized water to prepare a PVA solution. To the PVA solution, a powdered Cu (II)-bound exchange resin was added. The exchange resin used was an Amberlite® IR-120 H$^+$ cation exchange resin (commercially available from the Dow Chemical Company). The bound resin was prepared by soaking 2 grams of resin beads in 250 mL of 0.02 M of $Cu(SO_4)_2$ solution for 48 hours. The process was repeated once more and then the resin beads were washed with deionized water, dried and milled into a fine powder. The fine powder was added to the PVA solution to form the calcium hardness reagent suspension.

Deposition Procedure

A portion of the calcium hardness reagent suspension was deposited on a carbon working electrode present on an electrochemical sensor having a reference electrode and a counter electrode. The total amount of the suspension deposited on the working electrode was about 7.14 µL. Once deposition procedure was completed, the electrochemical sensor was carefully placed in an oven at 100° C. for 15 minutes. The sensor was removed from the oven and allowed to cool for a period of time of at least 5 minutes.

Testing

Figure 6:
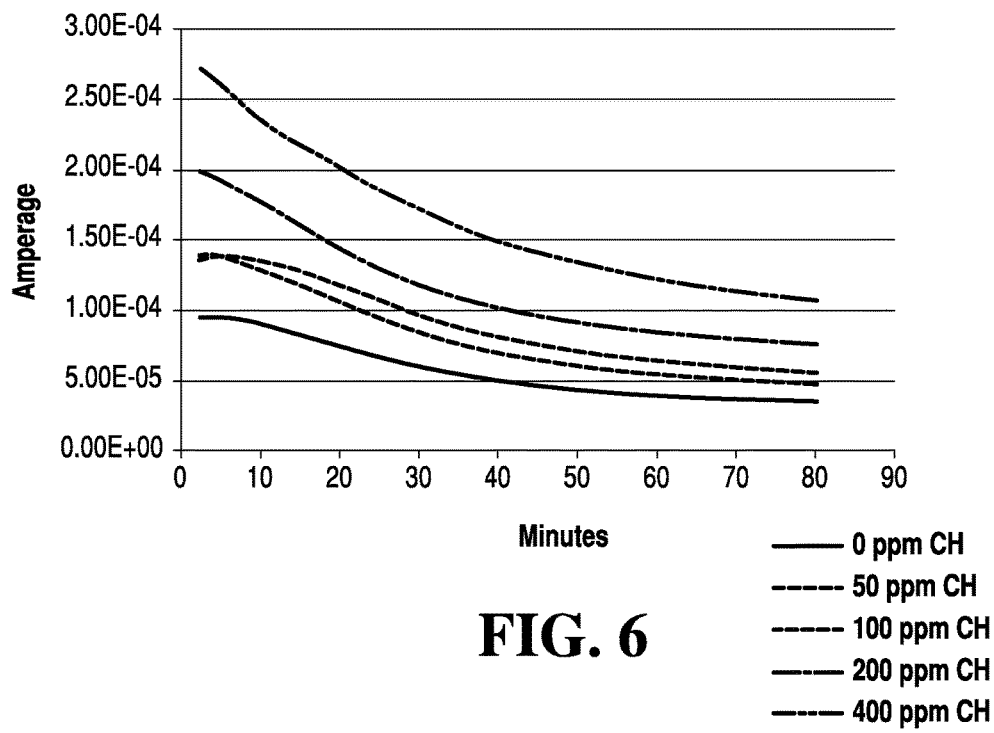
FIG. 6 shows a plot graph of calcium hardness detected over time with the electrochemical sensor of the invention.

The calcium hardness sensor was evaluated using amperometric analysis against five (5) stock solutions with increasing levels of calcium ions to approximate increasing levels of calcium hardness in a pool of water: 0 ppm, 50 ppm, 100 ppm, 200 ppm and 400 ppm. The results are shown in FIG. 6.

F. Preparation and Testing of Cyanuric Acid (CYA) Sensor

Preparation of CYA Detection Reagent Solution

The CYA detection reagent composition was prepared by dissolving 0.1% by weight of polyvinyl alcohol (15 mg/15 mL) in deionized water to prepare a solution. To this solution, 10 ppm as Cu was added. The mixture was shaken until the components were dissolved. The resulting solution formed the CYA detection reagent solution.

Deposition Procedure

A portion of the CYA detection reagent solution was deposited on a carbon working electrode present on an electrochemical sensor having a reference electrode and a counter electrode. The total amount of the solution deposited on the working electrode was about 7.14 µL. Once deposition procedure was completed, the electrochemical sensor was carefully placed in an oven at 100° C. for 10 minutes. The sensor was removed from the oven and allowed to cool for a period of time of at least 5 minutes.

Testing

Figure 7:
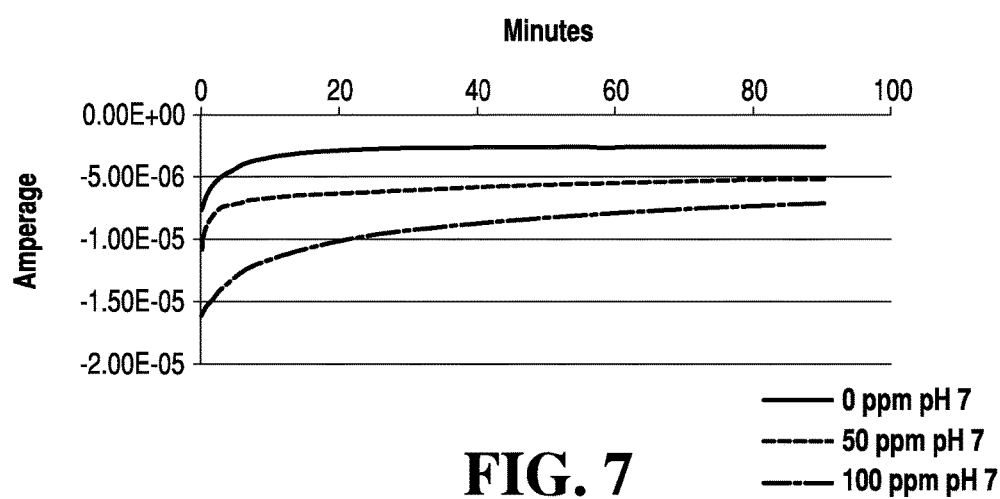
FIG. 7 shows a plot graph of cyanuric acid (CYA) over time detected with the electrochemical sensor of the invention.

The CYA detection sensor was evaluated using amperometric analysis against three (3) stock solutions with a pH of 7.6 and increasing levels of CYA to approximate increasing levels of CYA in a pool of water: 0 ppm, 50 ppm, and 100 ppm. The results are shown in FIG. 7.

G. Preparation and Testing of Copper Ion Sensor

Preparation of Copper Ion Detection Reagent Solution

The copper electrode modifying reagent composition was prepared by dissolving 0.1 M of potassium hydrogen phthalate (0.306 g) in 15 mL of deionized water. To this solution, 18% (v:v) of 0.1 M HCL was added to adjust the pH to about 3.5. The resulting solution formed the copper detection reagent solution.

Deposition Procedure

A portion of the copper detection reagent solution was deposited on a carbon working electrode present on an electrochemical sensor having a reference electrode and a counter electrode. The total amount of the solution deposited on the working electrode was about 7.14 µL. Once deposition procedure was completed, the electrochemical sensor was carefully placed in an oven at 100° C. for 10 minutes. The sensor was removed from the oven and allowed to cool for a period of time of at least 5 minutes.

Testing

Figure 8:
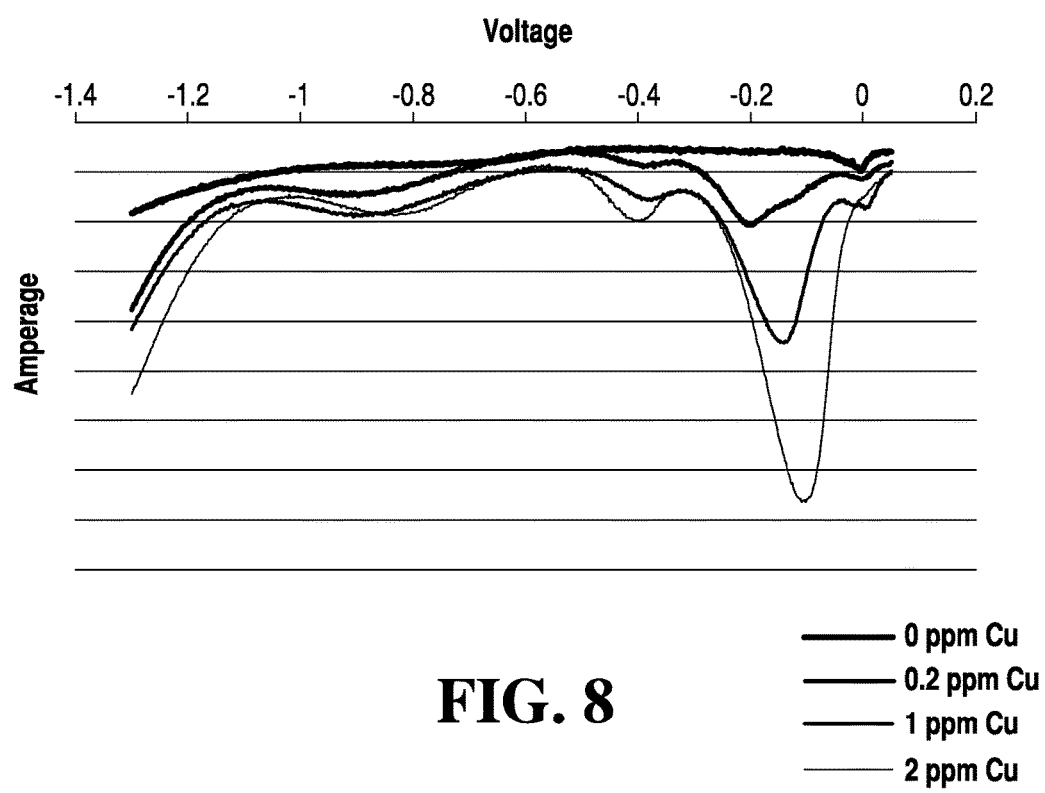
FIG. 8 shows a plot graph of dissolved copper detected over an increasing electric potential with the electrochemical sensor of the invention.

The copper ion detection sensor was evaluated using square wave voltammetry against four (4) stock solutions with increasing levels of copper to approximate increasing levels of copper in a pool of water: 0 ppm, 0.2 ppm, 1 ppm, and 2 ppm. The results are shown in FIG. 8.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A electrochemical sensor for the detection and analysis of cyanuric acid in water, the electrochemical sensor comprising:
   (i) an electrically non-conductive support;
   (ii) a plurality of electrodes on the support, each electrode comprising an electrode material and having a first surface and an opposite second surface, the first surface facing towards the support and the second surface facing away from the support, the plurality of electrodes comprising
      a. a reference electrode,
      b. a counter electrode, and
      c. a working electrode; and
   (iii) a reagent composition containing a reagent for detecting cyanuric acid applied directly to the second surface of the working electrode, such that the reagent composition essentially completely covers the second surface of the working electrode or dispersed throughout the electrode material of the working electrode;
   wherein the reagent composition comprises a transition metal salt as the reagent and a polymeric binding component for the reagent, and wherein the transition metal of the transition metal salt is copper; and
   wherein the polymeric binding component comprises sodium alginate, polyethylene glycol, polyvinyl alcohol, or polyvinylpyrrolidone.

2. The electrochemical sensor according to claim 1, comprising one to eight working electrodes.

3. The electrochemical sensor according to claim 1, wherein the reagent composition completely covers the entire second surface of the working electrode.

4. The electrochemical sensor according to claim 1, wherein the transition metal salt is selected from the group consisting of transition metal sulfates, transition metal nitrates and transition metal chlorides.

5. The electrochemical sensor according to claim 1, further comprising a plurality of electrical contacts, wherein each of the electrodes is electrically connected with a separate contact.

6. The electrochemical sensor according to claim 1, wherein the reference electrode comprises a silver/silver chloride electrode, the counter electrode comprises a carbon electrode and the working electrode comprises a carbon electrode.

* * * * *